(12) United States Patent
Kobayashi

(10) Patent No.: US 6,224,213 B1
(45) Date of Patent: May 1, 2001

(54) CORNEAL-SHAPED MEASURING APPARATUS

(75) Inventor: Nobuharu Kobayashi, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/538,480

(22) Filed: Mar. 30, 2000

(30) Foreign Application Priority Data

Mar. 30, 1999 (JP) .................................. 11-088060

(51) Int. Cl.[7] .................................................. A61B 3/10
(52) U.S. Cl. ............................................................ 351/212
(58) Field of Search .................................. 351/205, 211, 351/221, 246, 247; 606/4, 5

(56) References Cited

U.S. PATENT DOCUMENTS

| 5,300,965 | * | 4/1994 | Kitajima | 351/212 |
| 5,500,697 | | 3/1996 | Fujieda | 351/212 |
| 5,907,388 | * | 5/1999 | Fujieda | 351/211 |

FOREIGN PATENT DOCUMENTS

| 4-44736 | 2/1992 | (JP) | A61B/3/107 |
| 7-194551 | 8/1995 | (JP) | A61B/3/10 |
| 11-513580 | 11/1999 | (JP) | A61B/3/10 |
| 97/14351 | 4/1997 | (WO) | A61B/3/107 |

* cited by examiner

Primary Examiner—George Manuel
(74) Attorney, Agent, or Firm—Sughrue, Mion, Zinn, Macpeak & Seas, PLLC

(57) ABSTRACT

A corneal-shape measuring apparatus for measuring the shape of a cornea of an eye to be examined includes: a target plate formed of a transparent resin as its material and for projecting targets formed by light-transmitting portions and light-shielding portions onto a wide range of the cornea; a surface emitting plate for illuminating the targets from behind; an imaging optical system for picking up a target image formed on the cornea; a control unit and an image processing unit for analyzing the picked-up target image to determine the corneal shape; and an illuminating light source disposed to allow rays of light to be incident upon an end face of the target plate, wherein the target plate has the targets formed on its front surface facing the cornea, is provided with matte treatment of high reflectivity on a rear surface thereof, and is used jointly with the surface emitting plate.

13 Claims, 6 Drawing Sheets

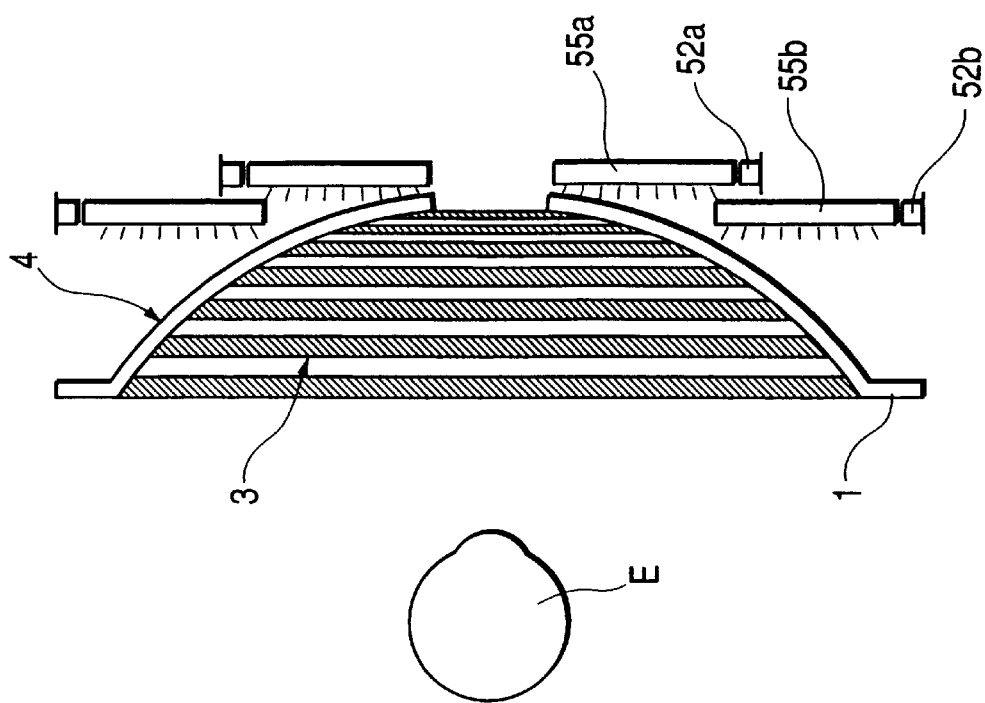
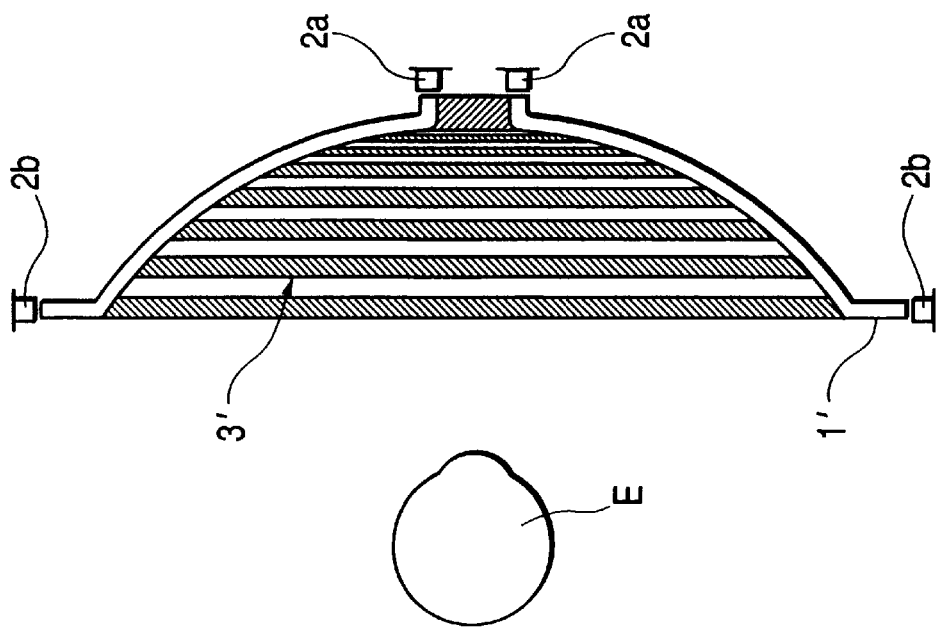

CORNEAL-SHAPED MEASURING APPARATUS

BACKGROUND OF THE INVENTION

1. Field of the Invention

The present invention relates to a corneal-shape measuring apparatus for measuring the shape of a cornea of an eye to be examined.

2. Description of the Related Art

An apparatus for measuring a corneal shape is known in which a multiplicity of ring pattern targets (indexes) are projected onto a cornea to be examined, a target (index) image formed on the cornea is picked up, and the corneal shape is measured on the basis of the picked-up image.

Conventionally, the projection of ring pattern targets (indexes) onto the cornea is effected by illuminating from behind a Placido plate having a target (index) portion on which annular light-transmitting portions and light-shielding portions (masking portions) are alternately formed concentrically, and its illuminating methods include those shown in FIGS. 7A to 7C.

In a method shown in FIG. 7A, an annular light source 101 constituted by a fluorescent lamp, a cold cathode-ray tube, a stroboscope tube, a neon tube, or the like is disposed in the rear of a Placido plate 100, an illumination space is provided in such a manner as to envelop the light source 101 by a reflecting member 102 and the Placido plate 100, and the light emitted from the light source 101 is reflected by the reflecting member 102, thereby making it possible to illuminate the Placido plate 100 efficiently.

In a method shown in FIG. 7B, instead of the annular light source 101 in FIG. 7A, a multiplicity of light-emitting diodes (LEDs) 103 are arranged annularly around an outer rim portion of the Placido plate 100, and the Placido plate 100 is illuminated by the reflection of the reflecting member 102.

In a method shown in FIG. 7C, a multiplicity of LEDs 111 are arranged annularly immediately behind the light-transmitting portions of a Placido plate 110 so as to effect illumination.

However, these illuminating methods have the following problems. In the case of the method shown in FIG. 7A, to illuminate the entire region of the Placido plate 100 uniformly, it is necessary to provide a relatively large illuminating space between the Placido plate 100 and the reflecting member 102, so that the apparatus becomes large in size. In addition, the Placido plate 100 formed of a resin can expand and deform due to heat generated from the annular light source 101, possibly reducing measurement accuracy. Although it is possible to form the Placido plate 100 of glass so as to prevent the deformation due to the thermal expansion, the apparatus becomes very expensive.

In the case of the method shown in FIG. 7B, the generation of heat can be suppressed by using the LEDs 103, but it is still necessary to provide a sufficiently large illuminating space between the Placido plate 100 and the reflecting member 102 in order to illuminate the entire region of the Placido plate 100, making the apparatus large in size. In addition, if the LEDs 103 are provided around the outer rim portion of the Placido plate 100 as shown in the drawing, the illumination of ring pattern targets (indexes) on the outer side of the Placido plate 100 is shaded, so that a large apparatus is required to project the ring pattern targets (indexes) over a wide range, and the clearance between the apparatus and the eye to be examined becomes short.

Further, since a difference in the quantity of light occurs in correspondence with the distance from each LED 103, it is difficult to illuminate the Placido plate 100 uniformly, and hence it becomes difficult to detect edges of the ring pattern targets (indexes) projected onto the cornea, leading to a decline in the measurement accuracy.

In the case of FIG. 7C, since the LEDs 111 must be arranged annularly for the respective light-transmitting portions of the Placido plate 110, the LEDs 111 are required in a large quantity, and these LEDs 111, combined with a power source therefor, make the apparatus very expensive.

SUMMARY OF THE INVENTION

In view of the above-described problems of the conventional art, it is an object of the present invention to provide a corneal-shape measuring apparatus which can be made compact without requiring a large illuminating space and which is capable of uniformly projecting ring pattern targets (indexes) with a simple arrangement at low cost.

The present invention provides the followings:

(1) A corneal-shape measuring apparatus for measuring the shape of a cornea of an eye to be examined, comprising:
   a target plate formed of a transparent resin as material thereof and for projecting a target formed by a light-transmitting portion and a light-shielding portion onto a wide range of the cornea;
   a surface emitting plate for illuminating the target from behind;
   an imaging optical system for picking up a target image formed on the cornea; and
   processing means for analyzing the picked-up target image to determine the corneal shape.

(2) The corneal-shape measuring apparatus according to (1), further comprising:
   an illuminating light source disposed to allow rays of light to be incident upon an end face of said target plate,
   wherein said target plate has the target formed on its front surface facing the cornea, is provided with matte treatment in a color of high reflectivity on a rear surface thereof, and is used jointly with said surface emitting plate.

(3) The corneal-shape measuring apparatus according to (2), wherein said illuminating light source includes a light-emitting diode.

(4) The corneal-shape measuring apparatus according to (2), wherein the matte treatment includes a white matte coating.

(5) The corneal-shape measuring apparatus according to (2), wherein the matte treatment includes a white diffusing film.

(6) The corneal-shape measuring apparatus according to (5), wherein said white diffusing film has dot-shaped regions which have reflectivity different from that of white diffusing regions thereof and whose density differs relative to a distance from said illuminating light source.

(7) The corneal-shape measuring apparatus according to (1), wherein said surface emitting plate comprises:
   a plurality of plate members formed of a transparent resin as material thereof and provided with matte treatment in a color of high reflectivity on rear surfaces thereof; and
   illuminating light sources arranged so as to cause the rays of light to be incident upon end faces of said plate members.

(8) The corneal-shape measuring apparatus according to (7), wherein said illuminating light sources include light-emitting diodes.

(9) The corneal-shape measuring apparatus according to (7), wherein the matte treatment includes a white matte coating.

(10) The corneal-shape measuring apparatus according to (7), wherein the matte treatment includes a white diffusing film.

(11) The corneal-shape measuring apparatus according to (10), wherein said white diffusing film has dot-shaped regions which have reflectivity different from that of white diffusing regions thereof and whose density differs relative to a distance from said illuminating light source.

(12) The corneal-shape measuring apparatus according to (7), wherein said plurality of plate members include at least conical plate members.

(13) The corneal-shape measuring apparatus according to (7), wherein said plurality of plate members include a plurality of flat, annular plate members of different diameters.

The present disclosure relates to the subject matter contained in Japanese patent application No. Hei. 11-88060 (filed on Mar. 30, 1999), which is expressly incorporated herein by reference in its entirety.

BRIEF DESCRIPTION OF THE DRAWINGS

FIG. 5A is a schematic diagram illustrating a modification of the apparatus;

FIG. 5B is a schematic diagram illustrating another modification of the apparatus;

DESCRIPTION OF THE PREFERRED EMBODIMENT

Figure 1:
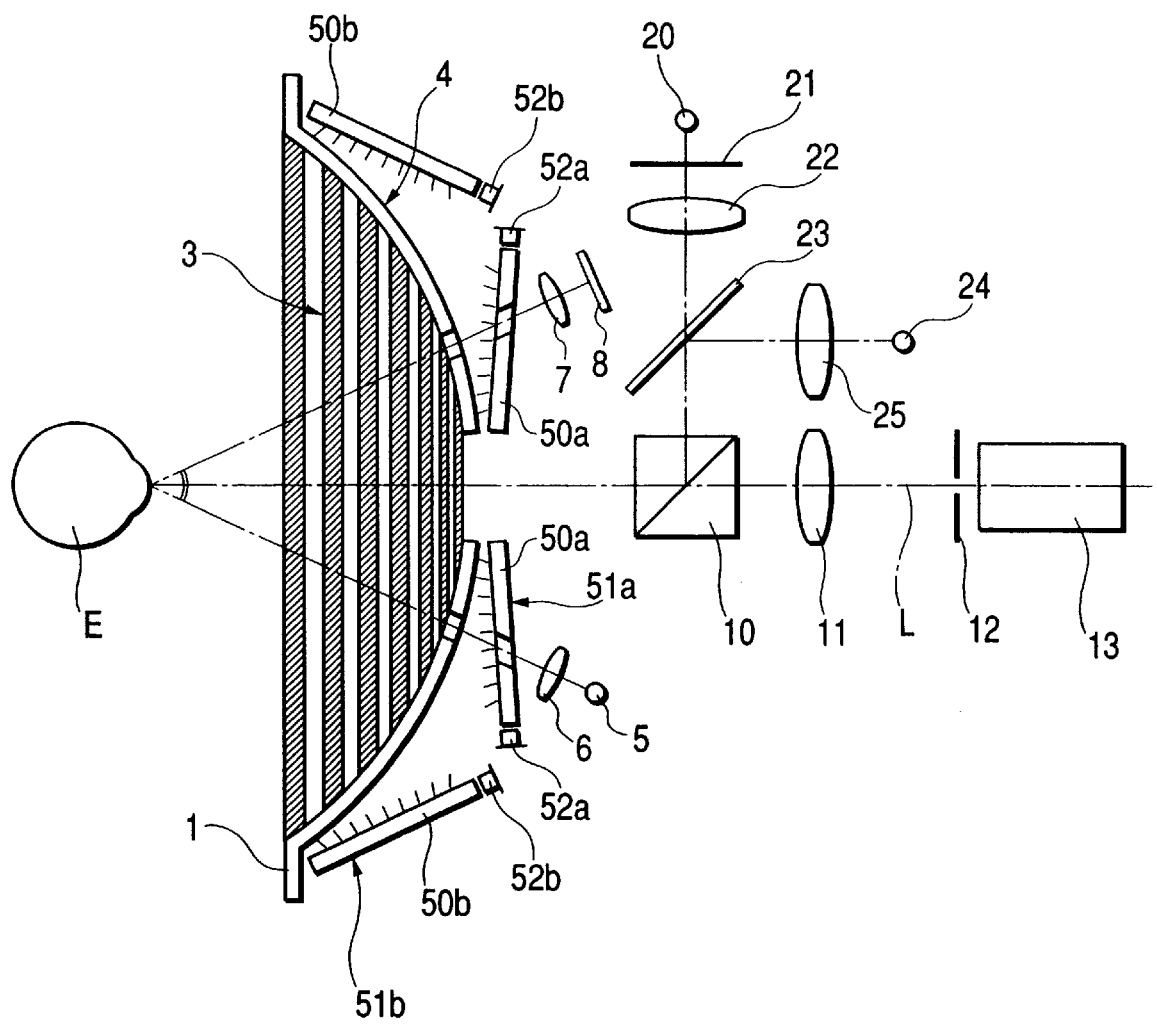
FIG. 1 is a schematic diagram of an optical system of a corneal-shape measuring apparatus in accordance with an embodiment of the invention.
Figure 2:
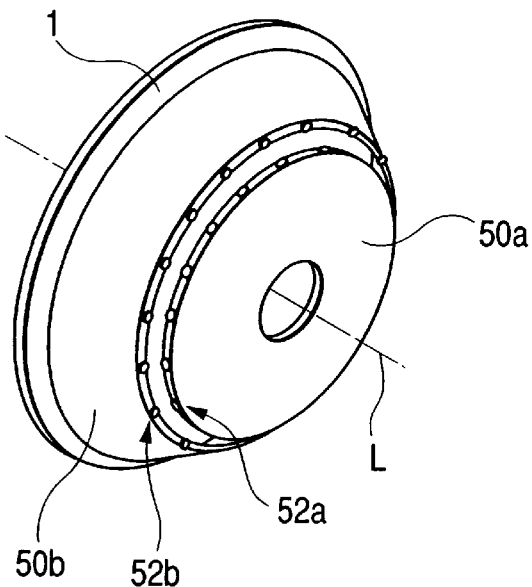
FIG. 2 is a schematic diagram illustrating a Placido plate and a surface emitting plate.

Referring now to the accompanying drawings, a description will be given of an embodiment of the invention. FIG. 1 is a schematic diagram of an optical system of a corneal-shape measuring apparatus in accordance with the invention, and FIG. 2 is a schematic diagram illustrating a Placido plate and a surface emitting plate.

A Placido plate 1 of a substantially semispherical shape is formed of a transparent resin such as an acrylic resin, and an opening is formed in its center. An outer rim portion of the Placido plate 1 has the shape of being bent in a chevron shape as illustrated in the drawings. A target (index) portion 3 having ring pattern targets (indexes) for measurement of the corneal shape is provided on a front surface (on the side of an eye to be examined) of the Placido plate 1. The ring pattern targets (indexes) are arranged such that a multiplicity of annular light-transmitting portions 3a and light-shielding portions (masking portions) 3b are formed alternately concentrically around an optical axis L of measurement. The light-transmitting portions 3a are formed as diffusing surfaces so as to allow the emergent light transmitted through the light-transmitting portions 3a to be converted to uniformly diffused light. The light-shielding portions 3b (including the surface of the chevron-shaped portion of the outer rim portion) are shielded from light by a black matte coating. In addition, a rear surface 4 of the Placido plate 1 is formed as a diffusing surface (frosted surface).

Reference numerals 50a and 50b denote two surface emitting plates of conical shapes, and these surface emitting plates 50a and 50b are arranged in such a manner as to surround the rear surface of the Placido plate 1 and cover the projection area of the target (index) portion 3 formed on the surface of the Placido plate 1. The surface emitting plates 50a and 50b are formed of a transparent acrylic resin. Their rear surfaces 51a and 51b are provided with a white matte coating for diffusely reflecting the light. A multiplicity of LEDs 52a are arranged circumferentially around an outer peripheral end face of the inner surface emitting plate 50a, while a multiplicity of LEDs 52b are similarly arranged circumferentially around an inner peripheral (rear) end face of the outer surface emitting plate 50b.

The light emitted from the LEDS 52a is guided into the interior of the surface emitting plate 50a, and the obverse surface of the surface emitting plate 50a undergoes surface emission as the light is diffusely reflected by the rear surface 51a, thereby illuminating the rear surface 4 of the Placido plate 1. Similarly, the surface emitting plate 50b also illuminates the rear surface 4 of the Placido plate 1. Since the illuminating light is further diffused by the diffusing surface of the rear surface 4, the target (index) portion 3 can be illuminated uniformly. As a result, the ring pattern targets (indexes) whose difference between light and shade is small are projected onto an eye E to be examined.

Incidentally, since the LEDs (52a, 52b) are disposed on one end faces of the surface emitting plates 50a and 50b, a slight difference in luminance occurs as the distance from the LED is farther away. Accordingly, the surface emitting plate whose distance is farther away from the LEDs is disposed closer to the Placido plate 1 so as to overcome this problem. Namely, by changing the spatial distance between the surface emitting plate (50a, 50b) and the Placido plate 1 in correspondence with the luminous intensity which varies at the portion of the surface emitting plate (50a, 50b), the irregularity of illumination of the rear surface 4 of the Placido plate 1 can be alleviated, with the result that the illumination can be easily made uniform.

Figure 3:
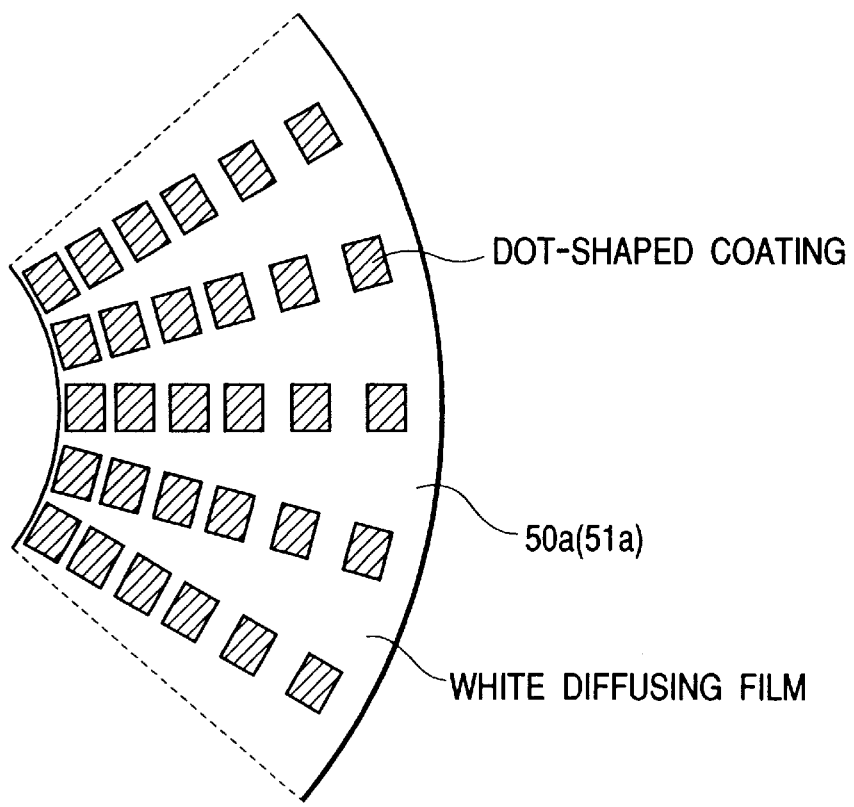
FIG. 3 is a schematic explanatory diagram of a white diffusing film and a dot-shaped coating.

It should be noted that the rear surfaces 51a and 51b of the surface emitting plates 50a and 50b may be provided with a white diffusing film on which paint having reflectivity different from that. of the white diffusing film is coated in dot form (see FIG. 3), instead of the white matte coating. In this case, if the density of the dots is varied in correspondence with the distance from the LED (52a, 52b) which is the illuminating light source, the reflectivity of the rear surfaces 51a and 51b can be changed. Therefore, even in a case where the LEDs are provided on only one side or the attenuation of the guided light emitted from the LEDs is large, the target (index) portion 3 of the Placido plate 1 can be illuminated substantially uniformly. In the dot-shaped coating, specular gloss paint may be used instead of the diffusible matte paint. For instance, paint having higher reflectivity than the white diffusing film is applied in dot form. The farther the distance from the LED, the higher the dot density, i.e., the higher the reflectivity per unit area.

Hence, since the reflectivity is increased in correspondence with the attenuation of the light intensity, the target (index) portion 3 can be illuminated uniformly. The reflecting portions in dot form can be easily formed by silk-screen printing or the like.

It should be noted that the Placido plate 1 need not be colorless and transparent, and may be a transparent plate colored in red or the like, or may be provided with a coating or the like having wavelength selectivity to allow its surface (light-transmitting portion) to transmit only a particular wavelength therethrough.

In FIG. 1, a working-distance detecting optical system is disposed in the rear of the Placido plate 1, and is comprised of a target- (index-) projecting optical system including a light source 5 emitting infrared light and a lens 6, as well as a target-(index-) detecting optical system including a lens 7 and a position detecting element 8. The light from the light source 5 is converted to a substantially parallel beam of light by the lens 6, passes through openings which are respectively provided in the Placido plate 1 and the surface emitting plate 50a, and is applied to the cornea of the eye E from a diagonal direction. The optical axis of detection of the target-(index-) detecting optical system is disposed so as to be symmetrical with the optical axis of projection of the target-(index-) projecting optical system, and the light emitted from the light source 5 and reflected by the cornea passes through the openings respectively provided in the Placido plate 1 and the surface emitting plate 50a and through the lens 7, and is incident upon the position detecting element 8. When the eye E undergoes relative movement in the back-and-forth direction (in the direction of the optical axis L), a target (index) image (bright spot) formed on the cornea also moves on the position detecting element 8, so that the state of alignment of the working distance of the eye E can be detected from its offset position.

A beam splitter 10, a lens 11, a diaphragm 12, and a CCD camera 13 are disposed on the optical axis L, thereby forming an imaging optical system. output signals from the camera 13 are used for the observation of an anterior portion of the eye E, the picking up of images of the ring pattern targets (indexes) projected on the cornea, and the detection of an alignment target (index) image in the vertical and horizontal directions, which will be described later.

Light from a fixation target (index) 21 illuminated by a fixation light source 20 for emitting visible light passes through a lens 22 and a dichroic mirror 23, is then reflected by the beam splitter 10 so as to be coaxial with the optical axis L, and is directed toward the eye E. Near infrared light emitted from a light source 24 for alignment is converted to a substantially parallel beam of light by a lens 25 and is projected onto the cornea of the eye E, thereby forming an alignment target (index) image (bright spot) for the vertical and horizontal directions. The dichroic mirror 23 has the properties of allowing the visible light from the fixation light source 20 to be transmitted therethrough and of reflecting the near infrared light from the light source 24 for alignment. The states of alignment of the optical axis L in the vertical and horizontal directions (X and Y directions) are detected on the basis of the position of the alignment target (index) image picked up by the camera 13.

Figure 4:
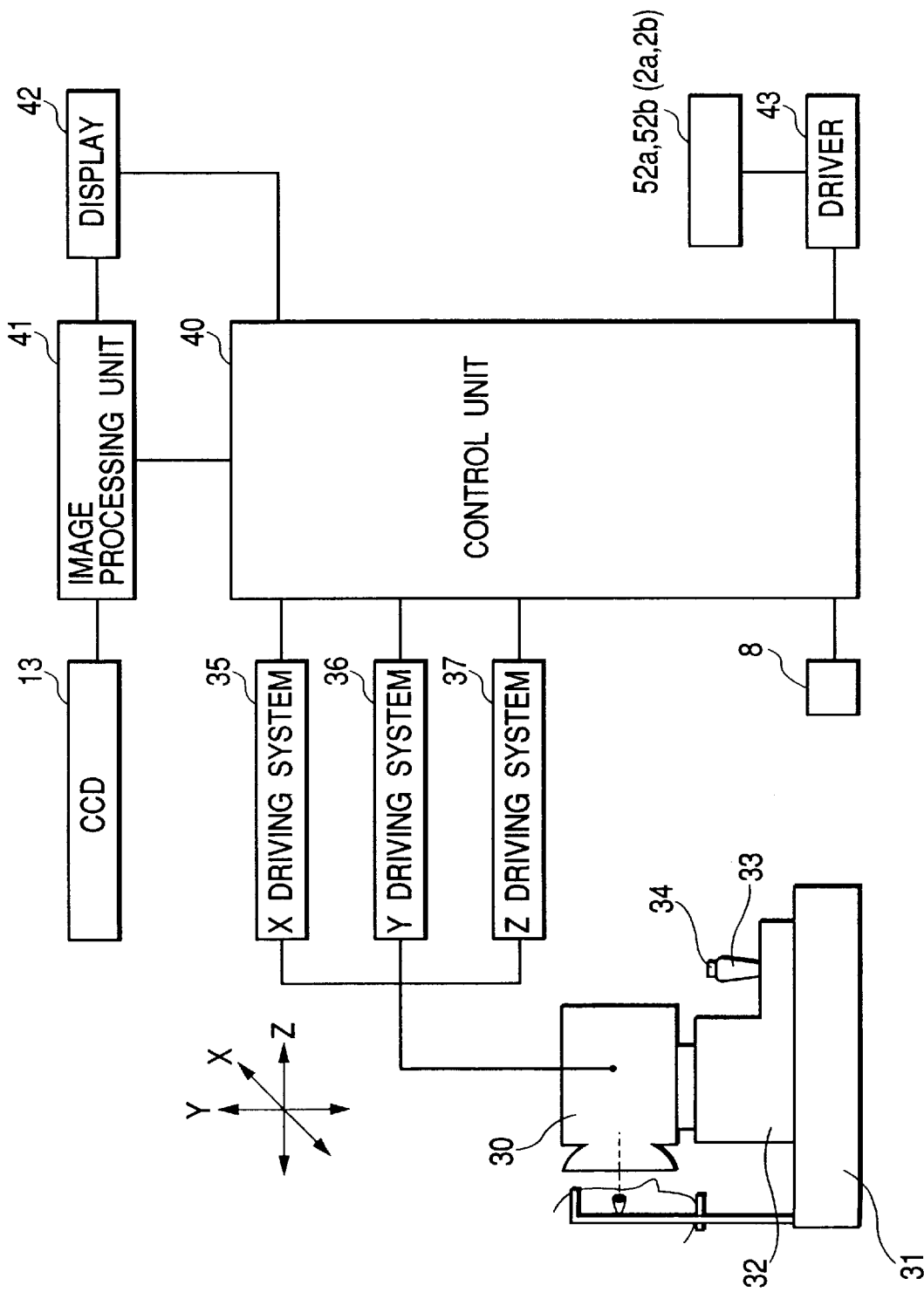
FIG. 4 is a block diagram illustrating the configuration of essential portions of a control system of the apparatus.

FIG. 4 is a block diagram illustrating the configuration of essential portions of a control system of the apparatus. A measurement unit 30, on which the optical system shown in FIG. 1 is disposed, is driven by an X driving system 35, a Y driving system 36, and a Z driving system 37 in the X direction (left-and-right direction), Y direction (vertical direction), and Z direction (back-and-forth direction), respectively, with respect to a movable carriage 32 which is slidable in the horizontal direction on a base 31. Incidentally, the movable carriage 32 is slid on the base 31 in the X and Z directions by the operation of a joystick 33. The driving systems 35, 36, and 37 are respectively constituted by motors, sliding mechanisms, and the like, and their drive is controlled by a control unit 40 for controlling the overall apparatus.

During observation, an image processing unit 41 detects an alignment target (index) image picked up by the camera 13, and inputs the result of detection to the control unit 40. On the basis of the detection signal inputted thereto, the control unit 40 determines the state of vertical and horizontal alignment of the apparatus (measurement unit 30) with respect to the eye E. In addition, when a trigger signal for imaging is inputted thereto, the image processing unit 41 fetches a ring pattern target (index) image (Placido-ring image) picked up by the camera 13, and subjects it to predetermined image processing for analyzing the corneal shape. The anterior image picked up by the camera 13, the results of analysis,. and the like are displayed on a display 42.

Next, a description will be given of the operation of the apparatus having the above-described configuration. The anterior image of the eye E picked up by the camera 13 is displayed on the display 42, and an examiner obtains rough alignment by operating the joystick 33 and the like while observing the anterior image displayed on the display 42. When a target (index) image formed by the light source 24 comes to be detected by the image processing unit 41, the control unit 40 moves the measurement unit 30 by controlling the drive of the X driving system 35 and the Y driving system 36 such that the X and Y directions of the measurement unit 30 are set in predetermined states of alignment. Further, when a target (index) image for detection of the working comes to be detected by the position detecting element 8, the control unit 40 controls the drive of the Z driving system on the basis of its detection signal so as to move the measurement unit 30 in the back-and forth direction so that its Z direction is set in a proper state. When the states of alignment in the X, Y, and Z directions become proper, respectively, the control unit 40 automatically issues a trigger signal to effect the picking up of a ring pattern target (index) image. Instead of being automatically issued by the control unit 40, the trigger signal may be issued by the pressing of a measurement switch 34 by the examiner.

The control unit 40 drives a driver 43 to light up the LEDs 52a and 52b. The target (index) portion 3 of the Placido plate 1 is illuminated as the LEDs 52a and 52b are lit up, so that the ring pattern targets (indexes) are projected onto the cornea. The image signal from the camera 13 is fetched into a frame memory of the image processing unit 41 in synchronism with the lighting up of the LEDs 52a and 52b. During the fetching of the image, if the alignment target (index) image is noise, the light sources 5 and 24 may be turned off.

The image processing unit 41 obtains a corneal shape by effecting predetermined analysis processing such as the edge processing of each ring pattern target (index) image on the basis of the images fetched into the frame memory (refer to U.S. Pat. No. 5,500,697 (JP-A-7-124113), for example). In the projection of the ring pattern targets (indexes), since the uniform illumination of the target (index) portion 3 is possible by the illumination of the Placido plate 1 as described above, ring pattern targets (indexes) with a small difference between light and shade are projected on the cornea, so that edge detection can be effected with high accuracy. Accordingly, results of analysis with high accuracy can be obtained. The results of analysis are displayed on the display 42 as a topography (equal refractive power diagram), for example.

Next, referring to FIGS. 5A and 5B, a description will be given of modifications of the invention. In FIG. 5A, an outer rim portion and an inner rim portion of a substantially semispherical Placido plate 1' are formed in the shape of being bent in a chevron shape, and a multiplicity of LEDs 2a and 2b which emit red light are arranged annularly at the respective ends of the Placido plate 1'. Since the LEDs 2b at the outer rim portion are disposed in such a manner as to be directed toward the optical axis L, the jutting out of the apparatus toward the eye E (enlargement of the apparatus) can be suppressed while enlarging the ring pattern targets (indexes) provided on the Placido plate 1', and the clearance between the apparatus and the eye E can be made long. Meanwhile, since the LEDS 2a at the inner rim portion are disposed in such a manner as to be directed toward the eye E, more ring pattern targets (indexes) can be provided on the central side of the Placido plate 1', so that it becomes easy to project the ring pattern targets (indexes) to the vicinity of the central portion of the cornea. A rear surface 4' of the Placido plate 1' is provided with a white matte coating (which may be a white diffusing film coated in dot form) so as to diffusely reflect the light guided into the interior of the Placido plate 1'.

Figure 6:
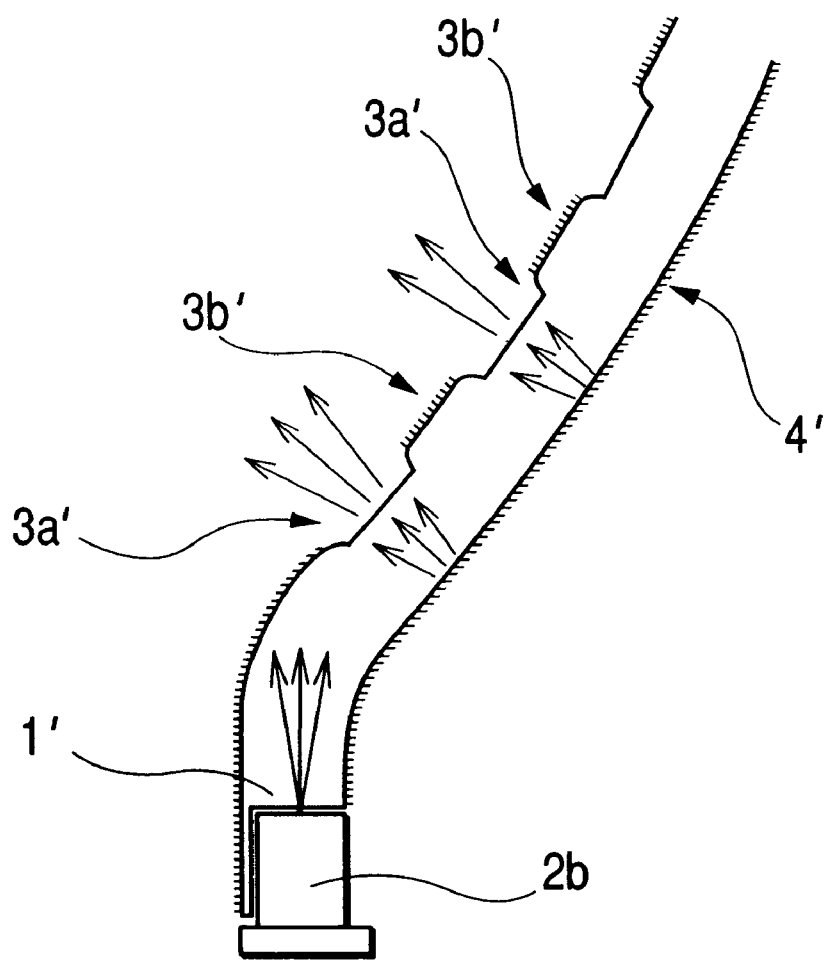
FIG. 6 is an enlarged view of an end portion of a Placido plate.
Figure 7C:
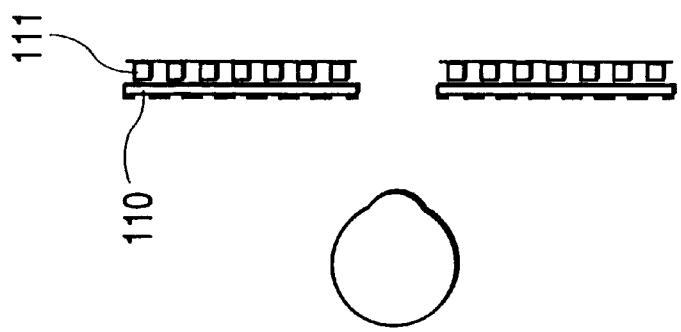
FIGS. 7A to 7C are schematic explanatory diagrams of conventional Placido plate illumination.
Figure 7B:
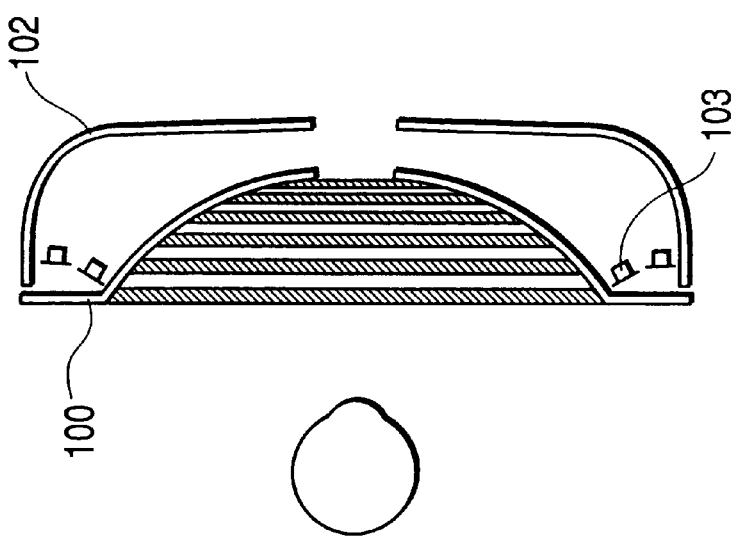
Figure 7A:
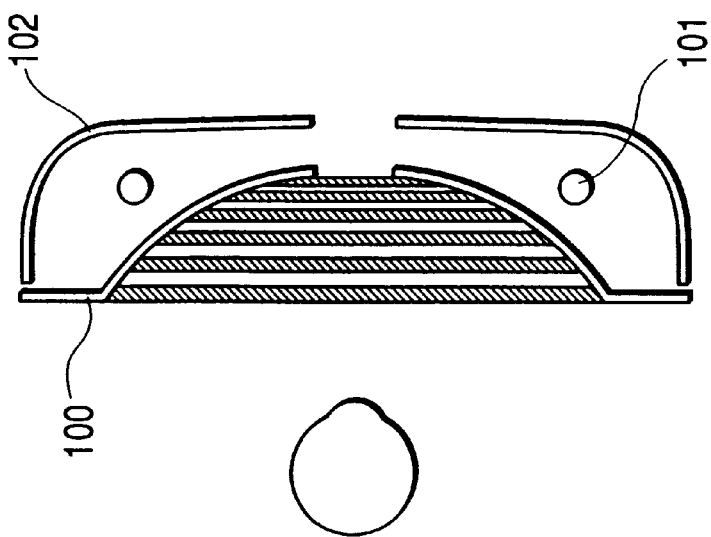

As shown in FIG. 6, the light emitted from the LEDs 2a and 2b is respectively made incident upon the interior of the Placido plate 1' from its respective ends, and is guided inside the Placido plate 1' while repeating reflection at the reverse surface of each light-shielding portion 3b' and reflection at the rear surface 4'. At this time, since the light guided in the interior is diffusely reflected by the white matte coating on the rear surface 4', the Placido plate 1' itself undergoes surface emission (the Placido plate 1' becomes a surface emitting plate). The entire surfaces of the ring pattern targets (indexes) provided on the front surface of the Placido plate 1' are illuminated by the diffuse reflection at the rear surface 4', and its illuminating light is diffused at light-transmitting portions 3a' and are emergent to the outside. Consequently, a multiplicity of concentric ring pattern targets (indexes) are projected onto the cornea.

The respective light emitted from the LEDs 2a and 2b is attenuated as it advances in the Placido plate 1'; however, since the LEDs (2a, 2b) serving as illuminating light sources are disposed at opposite ends of the Placido plate 1', the attenuated portions are offset by the mutual light, thereby making it possible to substantially uniformly illuminate a target (index) portion 3' of the Placido plate 1'.

It should be noted that if the inner surfaces of the light-shielding portions 3b', excluding the light-transmitting portions 3a', of the target (index) portion 3' are provided with a coating of high reflectivity, it is possible to enhance the conductivity of light incident upon the interior of the Placido plate 1'. Namely, since the light is reflected with high reflectivity at the inner surfaces of the light-shielding portions 3b', it is possible to suppress the attenuation of the quantity of light inside the Placido plate 1' until the light is emergent from the light-transmitting portions 3a', thereby making it possible to effect surface emission with high luminance.

In the case where the Placido plate is formed in which the target (index) portion and the surface emitting plate are thus formed integrally, since the indirect illuminating space is not required, it is possible to make the apparatus compact, and since the number of the component parts used is small, the apparatus can be manufactured at low cost.

In another modification shown in FIG. 5B which illustrates surface emitting plates 55a and 55b, an example is shown in which the surface emitting plates 50a and 50b shown in FIG. 1 are arranged in parallel, in which case the manufacture is facilitated since the surface emitting plats 55a and 55b can be fabricated in flat form. Various such modifications are possible by combining surface emitting plates of conical, cylindrical, disk, flat, and other similar shapes. As for the shape of the Placido plate, it is possible to use a conical or other similar shape instead of the semispherical shape, and it should be construed that arrangements having the same technological concept are included in the scope of the invention.

As described above, in accordance with the invention, it is possible to arrange an apparatus which can be made compact without requiring a large illuminating space, and which provides a long clearance between the apparatus and the eye to be examined.

In addition, also in the case where the LEDs are used as the illuminating light sources, the number of the LEDs used can be decreased, illumination with a wide measurable range can be realized, and the illumination of the ring pattern targets (indexes) can be easily made uniform. Furthermore, it is possible to ensure reproducibility of measurement by using the LEDs which generate small amounts of heat.

What is claimed is:

1. A corneal-shape measuring apparatus for measuring the shape of a cornea of an eye to be examined, comprising:

a target plate formed of a transparent resin as material thereof and for projecting a target formed by a light-transmitting portion and a light-shielding portion onto a wide range of the cornea;

a surface emitting plate for illuminating the target from behind;

an imaging optical system for picking up a target image formed on the cornea; and processing means for analyzing the picked-up target image to determine the corneal shape.

2. The corneal-shape measuring apparatus according to claim 1, further comprising:

an illuminating light source disposed to allow rays of light to be incident upon an end face of said target plate, wherein said target plate has the target formed on its front surface facing the cornea, is provided with matte treatment in a color of high reflectivity on a rear surface thereof, and is used jointly with said surface emitting plate.

3. The corneal-shape measuring apparatus according to claim 2, wherein said illuminating light source includes a light-emitting diode.

4. The corneal-shape measuring apparatus according to claim 2, wherein the matte treatment includes a white matte coating.

5. The corneal-shape measuring apparatus according to claim 2, wherein the matte treatment includes a white diffusing film.

6. The corneal-shape measuring apparatus according to claim 5, wherein said white diffusing film has dot-shaped regions which have reflectivity different from that of white diffusing regions thereof and whose density differs relative to a distance from said illuminating light source.

7. The corneal-shape measuring apparatus according to claim 1, wherein said surface emitting plate comprises:

a plurality of plate members formed of a transparent resin as material thereof and provided with matte treatment in a color of high reflectivity on rear surfaces thereof; and illuminating light sources arranged so as to cause the rays of light to be incident upon end faces of said plate members.

8. The corneal-shape measuring apparatus according to claim 7, wherein said illuminating light sources include light-emitting diodes.

9. The corneal-shape measuring apparatus according to claim 7, wherein the matte treatment includes a white matte coating.

10. The corneal-shape measuring apparatus according to claim 7, wherein the matte treatment includes a white diffusing film.

11. The corneal-shape measuring apparatus according to claim 10, wherein said white diffusing film has dot-shaped regions which have reflectivity different from that of white diffusing regions thereof and whose density differs relative to a distance from said illuminating light source.

12. The corneal-shape measuring apparatus according to claim 7, wherein said plurality of plate members include at least conical plate members.

13. The corneal-shape measuring apparatus according to claim 7, wherein said plurality of plate members include a plurality of flat, annular plate members of different diameters.

* * * * *